United States Patent [19]

Smith et al.

[11] 3,976,546

[45] Aug. 24, 1976

[54] CEPHALOSPORINS

[75] Inventors: Alan Smith, Ulverston; Ronald W. Larner, Swarthmoor, near Ulverston, both of England

[73] Assignee: Glaxo Laboratories Limited, Greenford, England

[22] Filed: Nov. 3, 1975

[21] Appl. No.: 628,057

[52] U.S. Cl. ................................. 195/29; 195/30; 195/66 R; 195/68
[51] Int. Cl.² ........................................ C12D 9/00
[58] Field of Search .................................. 195/29, 30

[56]  References Cited
UNITED STATES PATENTS 3,304,236  2/1967  Nuesch et al. .................... 195/29

3,912,589  10/1975  Smith et al. ..................... 195/30

*Primary Examiner*—Alvin E. Tanenholtz
*Attorney, Agent, or Firm*—Bacon & Thomas

[57] ABSTRACT

3-Acyloxymethylceph-3-em-4-carboxylic acids, for example cephalosporin C, are enzymically deacylated to their 3-hydroxymethyl analogues by means of esterases produced by culturing microorganisms or mutants thereof of the class Basidiomycetes, particularly of the genus Rhodosporidium, for example a microorganism of the species *Rhodosporidium toruloides*.

13 Claims, No Drawings

CEPHALOSPORINS

This invention relates to the transformation of cephalosporin compounds, and is particularly concerned with enzymically catalysed hydrolysis of 3-acyloxymethyl cephalosporins.

The cephalosporin compounds referred to in this specification are generally named with reference to "cepham" (J. Am. Chem. Soc. 1962, 84, 3400). The term "cephem" refers to the cepham structure with one double bond.

3-Hydroxymethyl cephalosporin compounds are valuable intermediates in the synthesis of a range of cephalosporin antibiotics possessing substituted methyl groups at the 3-position by virtue of the chemical reactivity of the hydroxyl group and the consequent ease with which the hydroxymethyl group may be converted to a desired 3-(substituted methyl) group. Furthermore, 7-acylamido-3-hydroxymethylceph-3-em-4-carboxylic acids possess antibiotic properties. The preparation of 3-hydroxymethyl cephalosporin compounds by hydrolysis of 3-acyloxymethyl cephalosporins, in particular naturally-occuring fermentation-produced 3-acetoxymethyl cephalosporin compounds such as cephalosporin C [(6R, 7R)-3-acetoxymethyl-7-(D-5-carboxypentanamido)ceph-3-em-4-carboxylic acid] and derivatives thereof, e.g. N-protected derivatives and compounds in which the D-5-amino-5-carboxypentanoyl group has been otherwise transformed or has been removed and if desired replaced by another acyl group, is accordingly of considerable interest.

Hydrolysis of 3-acyloxymethylceph-3-em-4-carboxylic acids to their 3-hydroxymethyl analogues by chemical methods has proved to be generally impractical, since such reactions are accompanied by rapid and substantially irreversible lactonisation involving reaction of the 3-hydroxymethyl and 4-carboxy groups and/or by destruction of the β-lactam ring system.

It has been found possible, however, to hydrolyse 3-acyloxymethylceph-3em-4-carboxylic acids by enzymically catalysed methods under conditions where lactonisation and β-lactam degradation may be substantially or completely obviated. While esterases derived from a range of sources, e.g. plant sources, may be employed in these enzymically catalysed methods, practical difficulties may be encountered in the isolation of sufficient quantities of esterase from some of the sources; esterases obtained from microorganisms are accordingly the most convenient in practice in view of the comparative ease with which microorganisms may be cultivated on a large scale using standard fermentation techniques to afford a ready supply of the esterase.

The present invention is based on our discovery that esterases obtained from certain microorganisms of the class Basidiomycetes promote hydrolysis of 3-acyloxymethylceph-3-em-4-carboxylic acids to their 3-hydroxymethyl analogues.

According to one aspect of the present invention, therefore, we provide a process for the conversion of a 3-acyloxymethylceph-3-em-4-carboxylic acid to a 3-hydroxymethyl analogue thereof by hydrolysis characterised in that the hydrolysis is catalysed by an esterase produced by culturing a microorganism of the class Basidiomycetes which is capable of generating the required esterase activity.

3-Acyloxymethylceph-3-em-4-carboxylic acids which may be hydrolysed in accordance with the invention include compounds represented by the general formula

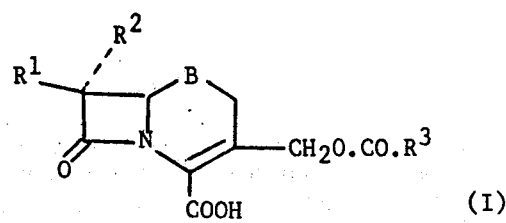

wherein $R^1$ is an amino or blocked amino group, for example a $C_{1-20}$ carboxylic acylamido group; $R_2$ is hydrogen or a lower alkyl, lower alkoxy, lower alkylthio or lowr alkanoyl group (the term "lower" as used herein designating groups containing not more than 8, preferably not more than 6 carbon atoms); $R^3.CO$ is a $C_{2-20}$ carboxylic acyl group; and B is $> S$ or $> S \rightarrow O$ (α- or β- ).

Acylamido groups $R^1$ which may be present in the compounds of formula I include the D-5-amino-5-carboxypentanamido group found in naturally-occuring fermentation-produced compounds such as cephalosporin C; N-protected derivatives of the D-5-amino-5-carboxypentanamido group, e.g. wherein the amino group is substituted by a protecting group of the type described in any of British Patent Specifications Nos. 1,041,985; 1,302,015 or 1,313,207, for example a lower alkyl group, an aryl lower alkyl group, an aryl group (e.g. 2,4-dinitrophenyl) or an acyl group, particularly a lower alkanoyl group (e.g. acetyl, propionyl or butyryl), an α-halo- or α,α-dihalo-lower alkanoyl group (e.g. chloroacetyl or dichloroacetyl), an aroyl group (e.g. benzoyl, chlorobenzoyl, nitrobenzoyl or tosyl), a lower alkoxycarbonyl group (e.g. t-butoxycarbonyl), an aryl lower alkoxycarbonyl group (e.g. benzyloxycarbonyl) or a di-acyl group such as phthaloyl; an acylamido group obtained by transformation of the D-5-amino-5-carboxypentanamido group, e.g. a 4-carboxybutamido group obtained therefrom by, for example, enzymic oxidation; formamido; a group of formula

where R is a carbocyclic or heterocyclic aryl group (e.g. phenyl; phenyl substituted by one or more of halo, hydroxy, lower alkyl, nitro, amino, lower alkanoyl, lower alkoxy or lower alkylthio; thienyl or furyl) or an aryloxy, arylthio, aryl lower alkoxy or aryl lower alkylthio group (e.g. phenoxy, phenylthio, 5-methyl-1,3,4-thiadiazol-2-ylthio or benzylthio) and $n$ is an integer of from 1 to 4; a group of formula

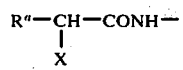

where $R^a$ is an aryl group (e.g. a monocylic or bicyclic carbocyclic aryl group such as phenyl, naphthyl, or phenyl substituted by one or more of halo, hydroxy, lower alkyl, nitro, amino, lower alkanoyl, lower alkoxy or lower alkylthio) and X is amino, protected amino (e.g. containing any of the N-protecting groups discussed above in connection with the D-5-amino-5-carboxypentanamido group, for example a t-butoxycarbonyl group), carboxy, carbalkoxy or hydroxy; and a group of formula

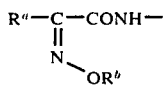

where $R^a$ has the above-defined meaning (e.g. where $R^a$ is phenyl, substituted phenyl, naphthyl, thienyl, furyl or pyridyl), and $R^b$ is hydrogen, acyl (e.g. lower alkanoyl), lower alkyl (e.g. methyl, ethyl, propyl or butyl), cycloalkyl (e.g. containing 5–7 carbon atoms, such as cyclopentyl or cyclohexyl), aryl (e.g. carbocyclic aryl such as phenyl) or aryl lower alkyl (e.g. benzyl or phenethyl). Examples of $R^1$ groups falling within the above general formulate which may be present in compounds of formula I include phenylacetamido, thienylacetamido, 2-hydroxy-2-phenylacetamido, 2-t-butoxy-carbonylamino-2-phenylacetamido and syn-2-furyl-2-methoxyiminoacetamido.

Acyl groups $R^3.CO$ which may be present in compounds of formula I include a range of aliphatic, araliphatic and aromatic groups, for example lower alkanoyl groups such as acetyl, propionyl and butyryl; lower alkenoyl, groups such as crotonoyl; aryl lower alkanoyl groups such as phenylacetyl; and aroyl groups such as benzoyl. As indicated above, the process of the invention finds particular application in the hydrolysis of cephalosporin C and derivatives thereof, i.e. compounds of formula I wherein $R^3.CO$ is an acetyl group.

The groups $R^2$ and B in formula I preferably represent hydrogen and >S repectively.

The level of the desired esterase activity generated by a particular microorganism of the class Basidiomycetes may readily be determined by, for example, preliminary small scall tests employing an appropriate 3-acyloxymethylceph-3-em-4-carboxylic acid substrate, e.g. cephalosporin C, the reaction system subsequently being assayed, e.g. by thin layer chromatography, to determine the amount of 3-hydroxymethylceph-3-em-4-carboxylic acid formed. The following method may, for example, be used for yeasts: the organism for test may be sub-cultured on a conventional nutrient medium e.g. an agar slant of medium comprising D-glucose (2%), yeast extract (1%), peptone (1%), potassium dihydrogen phosphate (0.5%) and agar powder (2%) which is incubated at 25°C for from 2–4 days.

An inoculum is transferred from the slope by sterile loop to a miniature flask containing medium (3 ml), comprising D-glucose (2.7%) yeast extract (1.3%), Oxoid peptone (1.3%), and potassium dihydrogen phosphate (0.7%), and an 8% solution of cephalosporin C potassium salt (1 ml). The flask, along with an uninoculated flask as control, is shaken at 25°C for three days and the contents then analysed by thin layer chromatography.

Samples of the flask contents (1 μl) and standards of cephalosporin C and its 3-hydroxymethyl analogue (1 μl of 20 mg/ml) are spotted on cellulose plates buffered to pH 5.8 – 6.0 with M/15 phosphate buffer and the plates are developed in 70% aqueous n-propanol. After drying, the plates are examined under ultra-violet light and the degree of deacetylation of the cephalosporin C qualitatively assessed by the intensity of the spots of starting material and 3-hydroxymethyl product from the flask contents.

For non-yeasts, the following slightly modified procedure may be used.

The organism for test is grown on an agar medium comprising maltose (4%), peptone (1%), malt extract (2.4%) and agar powder (2.5%) adjusted to pH 7.5 before sterilisation.

The slopes are incubated at 25°C for 7 days and an inoculum is transferred from each slope to a liquid medium (40ml) comprising glucose (2%), yeast extract (1%), peptone (1%) and potassium dihydrogen phosphate (0.5%) at pH 5.8. The culture is incubated at 25°C for 10 days on a shaker and used to inoculate a secondary liquid stage of the same medium with the addition of cephalosporin C (0.1%). After a further period of incubation for 3 to 8 days depending upon the rate of growth, the cultures are harvested.

Homogeneous suspensions of each culture are prepared by vigorous mixing using a mixer.

Reaction mixtures are set up comprising the homogeneous cell suspension (2 ml), 0.5 M potassium phosphate buffer pH 6.0 (2 ml) and a solution of cephalosporin C (3.33%; 6 ml) and are incubated for 5 days at 25°C with shaking Each sample is assayed by t.l.c. using cellulose-coated plates buffered to pH 5.8 to 6.0 and using a 70% v/v aqueous n-propanol solvent system. The presence of 3-hydroxymethyl cephalosporin product may be ascertained by UV irradiation of the t.l.c. plate.

Zones corresponding to authentic samples of (6R,7R)-7-(D-5-amino-5-carboxypentanamido)-3-hydroxy-methylceph-3-em-4-carboxylic acid (DAC) are eluted and the amount of DAC determined by optical density determination at 260 nm.

Organisms with no esterase activity do not produce a spot corresponding to the 3-hydroxymethyl compound.

Microorganisms of the class Basidiomycetes which may be useful as sources of the desired esterase activity include yeast microorganisms belonging to the order Ustilagenales or the family Sporobolomycetaceae. Yeast microorganisms in the Ustilagenales include organisms of the genera Leucosporidium and Rhodosporidium, for example strains of *Leucosporidium scottii*, *Rhodosporidium toruloides* and *Rhodosporidium spharerocarpum*. Yeast microorganisms in the Sporobolomycetaceae include organisms of the genera Bullera, Sporidiobolus and Sporobolomyces, for example strains of *Bullera alba, Bullera tsugae, Sporidiobolus johnsonii, Sporidiobolus ruinenii, Sporobolomyces roseus* and *Sporobolomyces salmonicolor*. Non-yeast microorganisms, of the class Basidiomycetes which generate the desired esterase activity may also be used. Representative of such microorganisms are smut fungi of the order Ustilagenales, e.g. strains of *Ustilago maydis*; microorganisms of the order Agaricales, e.g. strains of *Schizophyllum commune* and *Coprinus comatus*; and microorganisms of the order Polyporales e.g. strains of *Polyporus dichrous, Polyporus versicolor, Poria monticola*. Where non-yeast microorganims are to be employed it may be advantageous to select an organism which can be grown in submerged culture.

Yeast microorganisms of the genus Rhodosporidium, for example organisms of the species *Rhodosporidium toruloides* such as *Rhodosporidium toruloides* CBS 14 and *Rhodosporidium toruloides* CBS 349 and mutants thereof, are a particularly useful source of the desired esterase activity because of the high titre of the desired end product which they yield.

In general, the microorganism which is employed as the source of esterase activity may conveniently be preserved either by freeze drying a suspension of the organism in 2% skimmed milk, in sealed glass ampoules, or by regular subculturing of the microorganism onto solid media e.g. yeast extract/peptone/agar medium. The freeze dried culture may be reconstituted by the addition of sterile water. Freeze-drying is the preferred method for preserving the yeast cultures.

The resuspended organisms can be cultured by, for example, streaking onto a solid nutrient medium, e.g. an aqueous medium containing 2% glucose, 1% yeast extract, 1% peptone and 0.5% potassium dihydrogen phosphate, solidified with 2% agar (all percentages being w/v), at a pH of 5.6. The surface cultures are grown, e.g. at 25°C, until the agar is covered and may then be preserved for several months at low temperature e.g. 5°C. The organism may be grown in submerged culture, conveniently at 25°C, by, for example, inoculating a liquid nutrient medium containing a source of carbon, nitrogen and trace elements with a sample of the surface culture; an example of a suitable nutrient medium for this purpose is that described above for surface culture without the agar. It is often convenient to maintain a liquid culture of the organism which can be used to inoculate subsequent liquid cultures, e.g. production scale cultures, since this avoids the tedium of many surface to liquid inoculations and allows a larger inoculum to be used. The microorganism suspension obtained after incubation of such a subsequent liquid culture for an appropriate time, e.g. about 3 days, conveniently at 25°C, may then be used as a source of the esterase employed to deacylate the 3-acyloxymethylceph-3-em-4-carboxylic acid starting material. In the case of some organisms, e.g. *Leucosporidium scottii*, a lower incubation temperature, e.g. about 17°C, may be more convenient.

Formation of the esterase may in certain instances be enhanced by addition of an inducer to the liquid culture medium. Suitable inducers include cephalosporin C, cephalothin [(6R, 7R)-3-acetoxymethyl-7-(thien-2-yl) acetamidoceph-3-em-4-carboxylic acid] and their salts (e.g. alkali metal salts such as the potassium salt), inducers such as potassium cephalosporin C having been found effective in amounts of less than 0.1% w/v. The inducer is conveniently added to the liquid culture medium after sterilisation. The inducer may be sterilised by passage through a sterile filter, while the culture medium may be sterilised by, for example, autoclaving at about 121°C and 10,500 kg/m$^2$, e.g. for 15 minutes.

The esterase may be employed in several different forms to hydrolyse the 3-acyloxymethylceph-3-em-4-carboxylic acid starting material. Thus, for example, a sample of the liquid cultured medium may itself be employed as the source of esterase, if desired after rupture of the microorganism cells, for example by conventional methods such as ultrasonic treatment or treatment with lytic enzymes. An aqueous extract of the suspension resulting from such rupture of the cells may similarly be used. Alternatively, whole cells filtered off from the liquid cultured medium may be employed, as may the corresponding filtrate; where it is desired to use the filtrate the cells may again be ruptured, e.g. as described above, prior to filtration.

The use of whole cells is of particular advantage in that these may readily be separated, for example as a cell suspension, from the liquid cultured medium, are easily preserved, e.g. as a dried or deep frozen paste which may be added directly to the hydrolysis reaction mixture, and are easily removable, e.g. by filtration, from the reaction mixture after the hydrolysis has terminated. The cells thus separated may be reused, e.g. after washing with water, to hydrolyse further samples of the 3-acyloxymethylceph-3-em-4-carboxylic acid starting material; sufficient esterase activity to give a hydrolysed cephalosporin product of satisfactory quality in consistent yield may be retained throughout several recyclings of the cells.

If desired, the whole cells may be immobilized in or on an inert matrix (e.g. a polymer or a membrane), for example by covalent binding to an inorganic or organic polymer or by entrapment in or on a fibre (e.g. cellulose triacetate) or in an envelope such as a bead, prior to their addition to a hydrolysis reaction system, in order to protect the cells and minimise during their recycling. One preferred matrix for use in immobilization of the cells is polyacrylamide gel.

The esterase may also be employed in cell-free form, for example obtained by precipitation from a filtrate or cellular extract derived from the liquid cultured medium as hereinbefore described, using a suitable protein precipitant, for example a salt or a solvent. The precipitated cell-free esterase may, for example, be added directly to a hydrolysis reaction system or may be dissolved in water and added as an aqueous solution.

Alternatively the esterase may be employed in immobilized form, e.g. by insolubilisation or entrapment, on or in an inert matrix, suitable immobilized forms including those described in British Pat. No. 1,224,947 and Belgian Pat. No. 782,646. Thus, for example, an esterase obtained from an extract of the liquid cultured medium or from redissolution of precipitated esterase may be covalently bound to an otherwise inert inorganic or organic polymer, entrapped on or in a fibre (e.g. a fibrous polymer such as cellulose triacetate), or on or in a membrane or a polymer such as polyacrylamide gel, absorbed on an ion-exchange resin, or occluded in an envelope such as a bead. Immobilized esterases of these types may advantageously be employed in batch processes wherein the esterase is to be reused and in the hydrolysis of a continuous flow of 3-acyloxymethylceph-3-em-4-carboxylic acid by, for example, passage through a column containing the immobilized esterase.

The hydrolysis reaction is conveniently initiated by contacting the esterase with an aqueous medium containing the 3-acyloxymethylceph-3-em-4-carboxylic acid or a salt (e.g. an alkali metal salt such as the sodium or potassium salt) thereof, the medium conveniently containing 0.5 –10% w/v of the cephalosporin compound. The medium may if desired be sterilised prior to the hydrolysis, but we have found that the reaction may not require sterile conditions to be maintained and in such cases the hydrolysis may with advantage be carried out under non-sterile conditions.

Where the 3-acyloxymethylceph-3-em-4-carboxylic acid is a fermentation-produced cephalosporin, as in the case of cephalosporin C, the fermentation broth obtained from culture of the cephalosporin-producing organism (e.g. an organism of the genus Cephalosporium) may itself be treated with the esterase, obviating the need for an intermediate separation of the cephalosporin compound. Mycelium may if desired be removed from the broth before treatment, but in many instances it will be more convenient to employ the whole broth directly.

The hydrolysis may, for example, be carried out at a pH between 4 and 8. The pH may be maintained throughout the reaction by the use of buffer, e.g. phosphate buffer, for example to pH 6.0, though the addition of minor amounts of a strong base may also be necessary. The hydrolysis is conveniently effected at ambient temperature i.e. about 25°C, advantageously with stirring and/or aeration of the reaction mixture.

The amount of esterase or esterase-containing material required in a given reaction may be assessed by preliminary small-scale trial runs.

The time taken to effect complete deacylation of the 3-acyloxymethylceph-3-em-4-carboxylic acid will depend on the nature of the starting material and esterase on the reaction conditions employed. The course of the reaction may conveniently be followed by separating the product by thin-layer or paper chromatography using an appropriate support/solvent system combination and assaying densitometrically.

Where the 3-acyloxymethylceph-3-em-4-carboxylic acid starting material possesses a D-5-amino-5-carboxy-pentanamido group at the 7-position, as in the case of cephalosporin C, the hydrolytic deacylation process of the invention may be combined with enzyme catalysed oxidative deamination of the 7-position grouping, for example to a 4-carboxybutanamido grouping by treatment with a fungal oxidase, especially an oxidase derived from the yeast *Trigonopsis variabilis* as described in British Pat. No. 1,272,769 and Belgian Pat. No. 782,393. The enzymic transformation of the 3- and 7-position groupings may be effected either sequentially or concurrently.

The method used to isolate the 3-hydroxymethylceph-3-em-4-carboxylic acid product will depend on the nature of the product and the reaction system, but will in general employ conventional techniques. Thus, for example, if whole cells are used as the source of esterase these may be removed (and if desired recycled) by filtration or centrifugation and the solution further clarified by filtration, e.g. through a bed of kieselguhr. Where the 3-hydroxymethylceph-3-em-4-carboxylic acid is desacetyl cephalosporin C this may be isolated by, for example, desalting the solution by adsorption onto carbon followed by elution with acetone and water, further purifying the eluate by absorption onto an anion-exchange resin (for example Amberlite IRA-68 in the acetate form), eluting the desacetyl cephalosporin from the resin with potassium acetate solution and precipitating the product with acetone. Other techniques which may be employed in the isolation of different cephalosporin products include solvent extraction, acid precipitation, and precipitation at the isoelectric point (in the case of zwitterionic products such as (6R,7R)-7-amino-3-hydroxymethylceph-3-em-4-carboxylic acid).

The following examples serve to illustrate the invention. All temperatures are in °C, and the nature and purity of the products were investigated using the techniques, such as thin-layer chromatography (t.l.c), ultra-violet spectrophotometry (U.V.), infra-red spectrophotometry (IR), nuclear magnetic resonance (N.M.R.) and high pressure liquid chromatography (h.p.l.c.).

EXAMPLE 1

(6R,7R)-7-(D-5-Amino-5-carboxypentanamido)-3-hydroxymethylceph-3-em-4-carboxylic acid A solution of (6R,7R)-3-acetoxymethyl-7-(D-5-amino-5-carboxypentanamido)ceph-3-em-4-carboxylic acid, potassium salt (4 g) in dimineralised water (80 ml) was treated with a suspension (20ml) in 0.5 M pH 6.0 potassium phosphate buffer of cells obtained by culture of *Rhodosporidium toruloides* CBS 14 (40ml) (the microorganism having been cultured on the liquid yeast extract peptone medium as hereinbefore described for 72 hours, whereafter the cells were harvested by centrifugation and washed with water). The resulting mixture was maintained at 25° and shaken on a rotary shaker, the course of the reaction being monitored by thin layer chromatography. After 42 hours, when t.l.c. showed the deacetylation to be complete, the reaction mixture was centrifuged to remove solid matter and the resulting solution was treated with acetone (5 volumes). The precipitate which formed was recovered by centrifugation and dried under vacuum at room temperature to give the title compound (4.56 g). This was shown by t.l.c. on cellulose-coated plates using a 70% v/v aqueous n-propanol solvent system, comparing with an authentic sample and assaying densitometrically, to have a purity of about 53.3%, indicating an overall yield of 100%.

EXAMPLE 2

(6R,7R)-7-(D-5-Amino-5-carboxypentanamido)-3-hydroxymethylceph-3-em-4-carboxylic acid The process of Example 1 was repeated except that a suspension of cells obtained by culture of *Sporidiobolus johnsonii* CBS 5470 was used and the enzymically-catalysed deacetylation was allowed to proceed for 114 hours. 4.03 g of the title compound were obtained; this material had a purity of about 37.5%, indicating an overall yield of 63%.

EXAMPLE 3

(6R,7R)-3-Hydroxymethyl-7-(thien-2-ylacetamido)-ceph-3-em-4-carboxylic acid

A solution of sodium (6R,7R)-3-acetoxymethyl-7-(thien-2-ylacetamido)ceph-3-em-4-carboxylate (4 g) in demineralised water (80 ml) was treated with a suspension of cells obtained by culture of *Rhodosporidium toruloides* CBS 14, in a similar manner to that described in Example 1. Deacetylation was shown by t.l.c. to be complete after 42 hours, whereupon the reaction mixture was centrifuged to remove solid matter and the resulting solution was vigorously mixed with butyl acetate (200 ml). The pH of the mixture was adjusted to 2.2 – 2.5 by dropwise addition of concentrated phosphoric acid. The aqueous layer was separated and extracted with further butyl acetate (20 ml), a few drops of Gemex detergent being added to break the emulsion which formed. The butyl acetate fractions were combined and a 12.5% w/v solution of potassium acetate in industrial methylated spirit (≈8 ml) was slowly added thereto, until no further precipitation occurred. The precipitate was isolated by suction filtration, washed with a small volume of acetone and dried under vacuum at room temperature to give the title compound (2.87 g). This was shown by t.l.c. on cellulose-coated plates using an ethyl acetate - n-butanol - sodium acetate solvent system, comparing with an authentic sample and assaying densitometrically, to have a purity of about 75%, indicating an overall yield of 65%.

EXAMPLE 4

(6R,7R)-3-Hydroxymethyl-7-(thien-2-ylacetamido)-ceph-3-em-4-carboxylic acid

The process of Example 3 was repeated except that a suspension of cells obtained by culture of *Sporidiobolus johnsonii* CBS 5470 was used and the enzymically-catalysed deacetylation was allowed to proceed for 114 hours. 1.99 g of the title compound was obtained; this material had a purity of about 77%, indicating an overall yield of 46%.

Examples 5–9 illustrate methods which may be employed to test the level of the desired esterase activity generated by a particular microorganism.

EXAMPLE 5 a. A liquid yeast extract peptone nutrient medium as hereinbefore described, but additionally containing 2% w/v (6R,7R)-3-acetoxymethyl-7-(D-5-amino-5-carboxypentanamido) ceph-3-em-4-carboxylic acid, potassium salt, was inoculated with *Rhodosporidium toruloides* CBS 14 which had previously been cultured on an agar slant of the yeast extract peptone medium at 25° for 4 days. The liquid culture was incubated on a rotary shaker at 25° for 3 days. Samples of the culture medium were then subjected to t.l.c. on cellulose-coated plates, buffering to pH 5.8–6.0 with 0.067 M phosphate buffer and using a 70% v/v aqueous n-propanol solvent system. UV irradiation of each plate revealed the presence of a spot corresponding to authentic (6R,7R)-7-(D-5-amino-5-carboxypentanamido)-3-hydroxymethylceph-3-em-4-carboxylic acid.

b. The process of (a) was repeated except that (6R,7R)-3-acetoxymethyl-7-[2-(fur-2-yl)-2-methoxyiminoacetamido]ceph-3-em-4-carboxylic acid (syn isomer) was used in place of the (6R,7R)-3-acetoxymethyl-7-(D-5-amino-5-carboxypentanamido) ceph-3-em-4-carboxylic acid, potassium salt. T.l.c. examination of the liquid culture medium after incubation indicated the presence of (6R,7R)-7-[2-(fur-2-yl)-2-methoxyiminoacetamido]-3-hydroxymethylceph-3-em-4-carboxylic acid (syn isomer).

EXAMPLE 6

The processes of Examples 5(a) and (b) were repeated except that the *Rhodosporidium toruloides* CBS 14 was replaced by one of the following:

| | |
|---|---|
| *Rhodosporidium toruloides* | CBS 349 |
| *Rhodosporidium sphaerocarpum* | CBS 5939 |
| *Leucosporidium scottii* | CBS 5930 |
| *Sporidiobolus johnsonii* | CBS 5470 |
| *Sporobolomyces roseus* | CBS 486 |
| *Bullera alba* | CBS 501 |
| *Sporobolomyces salmonicolor* | CBS 496 |

In all cases either (6R,7R)-7-(D-5-amino-5-carboxypentanamido)-3-hydroxymethylceph-3-em-4-carboxylic acid or (6R,7R)-7-[2-(fur-2-yl)-2-methoxyiminoacetamido]-3-hydroxymethylceph-3-em-4-carboxylic acid (syn isomer) was detected as appropriate.

EXAMPLE 7

An inoculum of *Sporidiobolus ruinenii* CBS 5001 which had previously been cultured for 4 days at 25° on an agar slant of the yeast extract peptone medium hereinbefore described was incubated for 3 days at 25° in 40 ml of an aqueous medium containing 0.3% w/v yeast extract, 0.3% w/v malt extract, 0.5% w/v peptone and 1.0% w/v D-glucose. A portion of this liquid culture (1 ml) was then used to inoculate 53 ml of an aqueous medium containing 0.23% w/v yeast extract, 0.23% w/v malt extract, 0.38% w/v peptone, 0.75% w/v D-glucose and 1.96% w/v (6R,7R)-3-acetoxymethyl-7-(D-5-amino-5-carboxypentanamido)ceph-3-em-4-carboxylic acid, potassium salt. The resulting liquid culture was incubated for 5 days at 25° on a rotary shaker, whereafter t.l.c. examination of the culture medium using the method described in Example 5 indicated the presence of (6R,7R)-7-(D-5-amino-5-carboxypentanamido)-3-hydroxymethylceph-3-em-4-carboxylic acid.

EXAMPLE 8

The process of Example 7 was repeated except that the *Sporidiobolus ruinenii* CBS 5001 was replaced by *Bullera tsugae* CBS 5038. T.l.c. confirmed the production of (6R,7R)-7-(D-5-amino-5-carboxypentanamido)-3-hydroxymethylceph-3-em-4-carboxylic acid.

EXAMPLE 9

A liquid yeast extract peptone nutrient medium as hereinbefore described was inoculated with *Ustilago maydis* IMI 103761 which had previously been cultured for 72 hours at 25° on slopes of modified Sabouraud's agar. The liquid culture was incubated for 72 hours at 25° on a rotary shaker, whereafter a portion of the culture medium (1 ml) was incubated with 0.1 M phosphate buffer (8 ml) and 10% w/v (6R,7R)-3-acetoxymethyl-7-(D-5-amino-5-carboxypentanamido) ceph-3-em-4-carboxylic acid (1 ml) for 48 hours at 25° on a rotary shaker. Samples of the culture medium were then examined by t.l.c. on cellulose-coated plates using a 70% v/v aqueous n-propanol solvent system. UV irradiation of each plate revealed the presence of a spot corresponding to authentic (6R,7R)-7-(D-5-amino-5-carboxypentanamido)-3-hydroxymethylceph-3-em-4-carboxylic acid. The concentration of this material was 1.7 mg/ml compared with a concentration of 0.5 mg/ml obtained in control experiments in which no microorganism was employed.

EXAMPLE 10

(6R,7R)-7-[2-(fur-2-yl)-2-methoxyiminoacetamido]-3-hydroxymethylceph-3-em-4-carboxylic acid (syn isomer)

a. A medium containing glucose monohydrate (2.2%), Oxoid yeast extract (1%), Oxoid peptone (1%), potassium dihydrogen phosphate (1.5%), polypropylene glycol/white mineral oil (1/1) (0.1%) and cephalosporin C potassium salt (0.1%) was inoculated with a liquid culture of *Rhodosporidium toruloides* CBS14 (100 ml) and fermented for 32 hr. with agitation and aeration at 3 liters/min. Broth was harvested by centrifugation, supernatant liquor decanted and a mobile slurry obtained by adding demineralised water.

b. A reaction mixture consisting of (6R,7R)-7-[2-(fur-2-yl)-2-methoxyiminoacetamido]-3-acetoxymethylceph-3-em-4-carboxylic acid (syn isomer) (8.0 g), sodium hydroxide (2.6 g), demineralised water (120 ml), orthophosphoric acid (2.2 ml) and a slurry (18 ml) of *Rhodosporidium toruloides* CBS14 prepared as in (a) above was incubated at 25°C on an orbital shaker. After 20 hr. it was shown by t.l.c. (silica gel plates with 0.5M sodium chloride as solvent) that the reaction was complete. The reaction mixture was centrifuged, and the supernatant decanted and filtered through an asbestos pad. Methyl isobutyl ketone (14 ml) was added to the clear filtrate, the mixture was magnetically stirred and a 20% solution of orthophosphoric acid was added dropwise until the pH was 2.0. The mixture was then allowed to settle, the lower aqueous layer pipetted off and the solvent layer containing a copious white precipitate was vacuum filtered. The precipitate was washed with methyl isobutyl ketone (10 ml) and ice cold water (2 × 10 ml). The product was then sucked dry and dried in vacuo at room temperature to yield title compound (5.01 g). IR and NMR spectra of the product were consistent with it being title compound. The purity was estimated to be 92.2% by HPLC.

EXAMPLE 11

(6R,7R)-7-amino-3-hydroxymethylceph-3-em-4-carboxylic acid

A reaction mixture consisting of (6R,7R)-7-amino-3-acetoxymethylceph-3-em-4-carboxylic acid toluene-p-sulphonate (6.4 g), demineralised water (120 ml), ammonia solution (sg 0.880) sufficient to dissolve the cephalosporin and a slurry (12 ml) of *Rhodosporidium toruloides* CBS14 prepared as in Example 10(a) was adjusted to pH 6.5 with 20% orthophosphoric acid. The mixture was agitated on an orbital shaker at 25°C and after 20 hr, t.l.c. analysis (silica gel with 0.5M sodium chloride solution) revealed that the reaction was complete.

The reaction mixture was centrifuged, the supernatant decanted and filtered through an asbestos pad. The pH of the solution was then lowered to 3.6 by dropwise addition with stirring of 20% orthophosphoric acid and the resulting precipitate was filtered off and washed with ice cold water (5 ml) and acetone (10 ml).

A second crop was obtained from the filtrate by adding an equal volume of acetone. The resulting precipitate was filtered off and washed with water (10 ml) and acetone (20 ml). The two solids were dried separately in a vacuum oven at room temperature and combined to give title compound (1.99 g). NMR and IR spectra of the product were consistent with the title compound. The purity of the product was estimated to be 98.1% by HPLC.

EXAMPLE 12

Deacetylation of (6R,7R)-7-(D-5-benzoylamino-5-carboxypentanamido)-3-acetoxymethylceph-3-em-4-carboxylic acid The cell residue from the centrifugation of the reaction mixture of Example 10(b) was washed and a mobile slurry obtained by adding demineralised water. This slurry (18 ml) was added to a reaction mixture consisting of (6R,7R)-7-(D-5-benzoylamino-5-carboxypentanamido)-3-acetoxymethylceph3-em-4-carboxylic acid (8 g), sodium hydroxide (2.5g), demineralised water (180 ml) and orthophosphoric acid (sg 1.75, 2.2 ml) adjusted to pH 6.0. The mixture was incubated at 25°C on an orbital shaker for 21 hr. after which t.l.c. (silica gel plates with chloroform/methanol/formic acid, 48/8/2) revealed that the reaction was complete. After centrifuging the mixture and decanting the supernatant the product was characterised by reaction with diphenyldiazomethane, which yielded diphenylmethyl (6R,7R)-7-(D-5-benzoylamino-5-diphenylmethoxycarbonylpentanamido)-3-hydroxymethylceph-3-em-4-carboxylate (8.5 g) identical by IR and NMR spectroscopy with an authentic sample.

EXAMPLE 13

(6R,7R)-7-[2-(fur-2-yl)-2-methoxyiminoacetamido]-3-hydroxymethylceph-3-em-4-carboxylic acid (syn isomer)

A culture (60ml) of *Rhodosporidium toruloides* CBS 349 prepared by fermentation on a glucose/yeast extract/peptone medium similar to that described in Example 10(a) for three days in the presence of 0.1% cephalosporin C potassium salt was centrifuged and the cells re-suspended in water (25 ml). This suspension was added to a solution of (6R,7R)-7-[2-(fur-2-yl)-2-methoxyiminoacetamido]-3-acetoxymethylceph-3-em-4-carboxylic acid (syn isomer) (4.0 g), sodium hydroxide (1.3g) and orthophosphoric acid (1.1 ml) in demineralised water (30 ml). The reaction mixture was incubated on a shaker at 25°C for 23 hours, after which t.l.c showed that reaction was complete. The reaction mixture was then worked-up in a manner similar to Example 10 to yield title compound (2.5 g). The identity of the product was confirmed by t.l.c. and IR and NMR spectroscopy.

EXAMPLE 14

(6R,7R)-7-(D-5-amino-5-carboxypentanamido)-3-hydroxymethylceph-3-em-4-carboxylic acid A suspension of cells of Rhodosporium toruloides CBS 349 was prepared as in Example 13 with the cells suspended in 0.25M phosphate buffer, pH 6.0. To this yeast suspension (40 ml) was added a solution of cephalosporin C potassium salt (6.7g) in demineralised water (60 ml). The mixture was incubated for 20 hours on a shaker at 25°C, after which tlc showed that the reaction had gone to completion. The reaction mixture was worked-up in a manner substantially similar to that of Example 1, to yield the title compound (4.27g) with a $\lambda_{max}$ at 260 nm. The product behaved identically to an authentic sample of the title compound in t.l.c. systems. UV absorption indicated a purity of 45%.

EXAMPLE 15

(6R,7R)-3-Hydroxymethyl-7-[2-methoxyimino-2-(fur-2-yl)acetamido]ceph-3-em-4-carboxylic acid (syn isomer)

Sodium hydroxide (16.0 g) an orthophosphoric acid (13.5 ml) were dissolved in distilled water (750 ml). (6R,7R)-3-Acetoxymethyl-7-[2-methoxyimino-2-(fur-2-yl) acetamido]ceph-3-em-4-carboxylic acid (syn isomer ) (50g.), was added, and this dissolved to give a solution with a pH of 6.4. The pH was adjusted to 6.3 by addition of 20% orthophosphoric acid, and a suspension of Rhodosporidium toruloides CBS 14 cells (150 g.) was added. The mixture was stirred and aerated for 8 hours at 25° during which time M sodium hydroxide solution (105 ml.) had to be added to keep the mixture in the pH range 5.8 to 6.3. Thin layer chromatography showed that the conversion was complete. The mixture was stirred and aerated for a further 16 hours then the yeast removed by centrifugation. The yeast was washed by suspending in water (200 ml.) and recentrifuging. The main function was stirred with charcoal (2 g.) for 30 minutes then filtered through a Hyflo Supercel bed. The bed was washed with the yeast washings. Sodium chloride (250 g.) and 4-methylpentan-2-one (500 ml.) were added to the filtrate, and the pH was adjusted to 2.0 by addition of 20% orthophosphoric acid over 20 minutes. The mixture was cooled in an ice-bath during the acidification. The stirrer was stopped and the layers were allowed to settle. The clear aqueous layer was rejected and the precipitated solid was filtered off and washed with 4-methylpentan-2-one (50 ml) and water (3 × 40 ml.). The product was dried at 40° in vacuo for 24 hours to give the title compound as an off-white solid (38.39 g.) purity by h.p.l.c. 99.1%, total impurities by t.l.c. 2.5%.

EXAMPLE 16 a. (6R,7S)-3-Acetoxymethyl-7-methoxy-7-phenylacetamidoceph-3-em-4-carboxylic acid A cooled (−78°) solution of t-butyl (6R,7R)-3-acetoxymethyl-7-phenylacetamidoceph-3em-4-carboxylate (1.5 g.) in dry tetrahydrofuran (10 ml) was added over 3 minutes to a stirred and cooled (−78°) solution of lithium methoxide (358 mg) in dry methanol (8.8 ml) and tetrahydrofuran (50 ml) under nitrogen. t-Butyl hypochlorite (0.69 ml) was added after 3 minutes, and sitrring was continued for a further 5 minutes when the yellow solution was poured into a stirred mixture of ethyl acetate (150 ml) and water (150 ml) containing ammonium chloride (1 g) and sodium metabisulphite (1 g.). The aqueous phase was separated and extracted with ethyl acetate (50 ml) and the organic phases were combined and washed with brine (50 ml) and dried and evaporated to dryness in vacuo to give t-butyl (6R,7S)-3-acetoxymethyl-7-methoxy-7-phenylacetamidoceph-3-em-4-carboxylate (1.6 g).

A stirred solution of this product (1.6 g.) in trifluoroacetic acid (6.8 ml) and anisole (1.7 ml) was kept at ca. 23° and residual trifluoroacetic acid was removed by evaporation followed by a co-distillation with toluene (2 × 15 ml). A solution of the brown residue in sodium bicarbonate solution (25 ml) was stirred with ethyl acetate (25 ml) for 10 minutes. The aqueous layer was separated, adjusted to pH 2 with 2N-hydrochloric acid and extracted with ethyl acetate (3 × 25 ml). The extract was washed with brine and dried and evaporated to give a yellow solid (1.3 g.). A solution of this solid in acetone (50 ml) was treated with charcoal, the mixture was filtered, and the filtrate evaporated to dryness in vacuo. The Trituration of the residue with ether (25 ml) afforded the title acid (500 mg.) m.p. 167°–170°, $[\alpha]_D^{21}$ +190° (c 0.28, DMSO), $\lambda$max (0.1 M-pH 6 phosphate buffer) 265 nm ($E_{1cm}^{1\%}$ 196).

b. Sodium (6,R,7S)-3-acetoxymethyl-7-methoxy-7-phenylacetamidoceph-3-em-4-carboxylate A suspension of (6R,7S)-3-acetoxymethyl-7-methoxy-7-phenylacetamidoceph-3-em-4-carboxylic acid (200 mg) in water (3 ml) was adjusted to pH 6 by addition of saturated aqueous sodium bicarbonate. 0.4 M - pH 6 phosphate buffer (3 ml) was added, and the resulting solution was stirred with Rhodosporidium toroluides CBS 14 (1. g of frozen homogenate) at ca 20°. After 16 hours, examination by t.l.c. (chloroform-:methanol:acetic acid = 90:16:5) indicated complete conversion of the substrate. The mixture was clarified by centrifugation, and the supernatant liquid decanted off, and freeze-dried. Trituration of the residue with ether (10 ml) produced a colourless solid (400 mg) which was identified as containing the title compound by n.m.r. spectroscopy.

EXAMPLE 17 a. The organisums summarised in Table I were grown on an agar medium comprising maltose (4%), peptone (1%), malt extract (2.4%) and agar powder (2.5%) adjusted to pH 7.5 before sterilisation.

The slopes were incubated at 25°C for 7 days and an inoculum was transferred from each slope to a liquid extract (1%), peptone (1%) and potassium dihydrogen phosphate (0.5%) at pH 5.8. The culture was incubated at 25°C for 10 days on a shader and used to inoculate a secondary liquid stage of the same medium with the addition of cephalosporin C (0.1%). After a further period of incubation of 3 to 8 days depending upon the rate of growth, he cultures were harvested.

Homogeneous suspensions of each culture were prepared by vigorous mixing using a mixer.

Reaction mixtures were set up comprising the homogeneous cell suspension (2 ml), 0.5 M potassium phosphate buffer pH 6.0 (2 ml) and a solution of cephalosporin C (3.33%; 6 ml) and were incubated for 5 days at 25°C with shaking.

Each sample was assayed by t.l.c. using the method described in Example 5.

Zones corresponding to authentic samples of (6R,7R)-7-(D-5-amino-5-carboxypentanamido)-3-hydroxymethylceph-3-em-4-carboxylic acid (DAC) were eluted and the amount of DAC determined by optical density determination at 260 nm.

The results obtained are summarised in Table I.

b. The procedure of (a) above was repeated with (6R,7R)-7-[2-(fur-2-yl)-2-methoxyiminoacetamido]-3-acetoxymethylceph-3-em-4-carboxylic acid in place of cephalosporin C in the reaction mixture. The resulting 3-hydroxymethyl compound was assayed using the t.l.c. method of Example 10. The results obtained are summarised in Table I.

TABLE I

| Organism | Concentration of 3-hydroxymethyl compound in reaction mixture (mg/ml) | |
|---|---|---|
| | DAC | (6R,7R)-7-[2-(fur-2-yl)-2-methoxyiminoacetamido]-3-hydroxymethylceph-3-em-4-carboxylic acid |
| Polyporus dichrous CBS 446.50 | 7.7 | 8.5 |
| Polyporus versicolor CBS 471.72 | 7.7 | 9.2 |
| Poria monticola CBS 336.49 | 10.3 | 7.0 |
| Coprinus comatus CBS 150.39 | 10.3 | 9.5 |
| Schizophyllum commune CBS 103.20 | 9.1 | 7.3 |
| Control - no organism used | 4.0 | 4.6 |

We claim:

1. In a process for the enzymically catalysed hydrolysis of a 3-acyloxymethylceph-3-em-4-carboxylic acid to a 3-hydroxymethyl analogue thereof, the improvement which comprises contacting said 3-acyloxymethylceph-3-em-4-carboxylic acid with an esterase produced by culturing a microorganism of the class Basidiomycetes.

2. The process of claim 1 wherein said esterase is produced by culturing a yeast microorganism of the genus Rhodosporium.

3. The process of claim 2 wherein the microorganism is a strain of *Rhodosporidium toruloides*.

4. The process of claim 3 wherein the microorganism is *Rhodosporidium toruloides* CBS14.

5. The process of claim 3 wherein the microorganism is *Rhodosporidium toruloides* CBS 349.

6. The process of claim 1 wherein said esterase is produced bu culturing a yeast microorganism of the genera Leucosporidium, Ustilago, Bullera, Sporidiobolus and Sporobolomyces.

7. The process of claim 6 wherein the microorganism is a strain of *Leucosporidium scottii, Rhodosporidium sphaerocarpum, Bullera alba, Bullera tsugae, Sporidiobolous johnsonii, Sporidiobolus ruinenii, Sporobolomyces roseus, Sporobolomyces salmonicolor, Ustiligo maydis, Schizophyllum commune, Coprinus comatus, polyporus dichrous, polyporus versicolor,* and *Poris monticola*.

8. The process of claim 1 wherein said 3-acyloxymethylceph-3-em-4-carboxylic acid is a compound of general formula

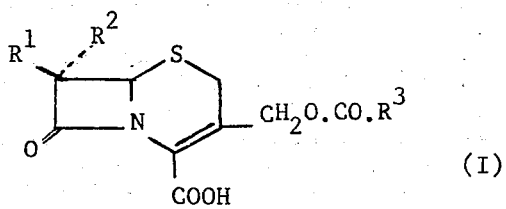

(I)

wherein R¹ is selected from amino, D-5-amino-5-carboxypentanamido, D-5-benzoylamino-5-carboxypentanamido, 4-carboxybutanamido formamido, a group of formula

R . CH₂ . CONH— where R is phenyl, thienyl or furyl; a group of formula

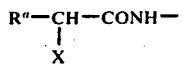

where $R^a$ is phenyl or naphthyl and X is amino, t-butoxycarbonylamino or hydroxy; and a group of formula

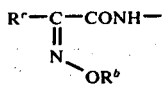

where $R^b$ is $C_{1-6}$ alkyl, $C_{5-7}$ cycloalkyl or phenyl and $R^c$ is phenyl, naphthyl, furyl, thienyl or pyridyl; $R^2$ is a hydrogen atom or a lower alkoxy group; and $R^3$ is methyl.

9. The process of claim 1 wherein the 3-acyloxymethylceph-3-em-4-carboxylic acid is contacted with a source of esterase comprising whole cells obtained from a cultured broth of the yeast microorganism.

10. The process of claim 1 wherein the 3-acyloxymethylceph-3-em-4-carboxylic acid is contacted with a source of esterase comprising a cultured broth of the yeast microorganism.

11. A process for the preparation of (6R,7R)-7-(D-5-amino-5-carboxypentanamido)-3-hydroxymethylceph-3-em-4-carboxylic acid which comprises contacting (6R,7R)-3-acetoxymethyl-7-(D-5-amino-5-carboxypentanamido) ceph-3-em-4-carboxylic acid with an esterase produced by culturing a yeast microorganism or a nutant thereof of the genus Rhodosporidium to effect enzymically catalysed hydrolysis thereof.

12. The process of claim 11 which comprises contacting a whole broth from a cephalosporin C fermentation with the esterase.

13. A process for the preparation of (6R,7R)-7-[2-(fur-2-yl) -2-methoxyiminoacetamido]-3-hydroxymethylceph-3-em-4-carboxylic acid (syn isomer) which comprises contacting (6R,7R)-3-acetoxymethyl-7-[2-(fur-2-yl)-2-methoxyiminoacetamido]ceph-3-em-4-carboxylic acid with an esterase produced by culturing a yeast microorgansim or a mutant thereof of the genus Rhodosporidium to effect enzymically catalysed hydrolysis thereof.

* * * * *

UNITED STATES PATENT AND TRADEMARK OFFICE
CERTIFICATE OF CORRECTION

PATENT NO. : 3,976,546
DATED : August 24, 1976
INVENTOR(S) : ALAN SMITH and RONALD W. LARNER It is certified that error appears in the above-identified patent and that said Letters Patent are hereby corrected as shown below:

On the title page, between lines 8 and 9, there should appear the following:

[30] Foreign Application Priority Data

November 8., 1974    Great Britain............48522/74

*Signed and Sealed this*

*Seventh* Day of *February 1978*

[SEAL]

*Attest:*

RUTH C. MASON      LUTRELLE F. PARKER
*Attesting Officer*      *Acting Commissioner of Patents and Trademarks*